United States Patent [19]

Feagin et al.

[11] Patent Number: 5,500,000
[45] Date of Patent: Mar. 19, 1996

[54] SOFT TISSUE REPAIR SYSTEM AND METHOD

[75] Inventors: John Feagin, Durham; Richard Glisson, Bahama, both of N.C.

[73] Assignee: United States Surgical Corporation, Norwalk, Conn.

[21] Appl. No.: 86,290

[22] Filed: Jul. 1, 1993

[51] Int. Cl.$^6$ .................................................. A61B 17/04
[52] U.S. Cl. .......................... 606/232; 606/224; 606/213; 606/220
[58] Field of Search .......................... 606/232, 60, 72–73, 606/79, 219, 213, 224; 24/453; 411/393

[56] References Cited

U.S. PATENT DOCUMENTS

| Re. 34,021 | 8/1992 | Mueller et al. ......................... 606/232 |
|---|---|---|
| 2,065,659 | 12/1936 | Cullen . |
| 3,570,497 | 3/1971 | Lemole . |
| 4,409,974 | 10/1983 | Freedland . |
| 4,696,300 | 9/1987 | Anderson . |
| 4,738,255 | 4/1988 | Goble et al. . |
| 4,741,330 | 5/1988 | Hayhurst . |
| 4,744,364 | 5/1988 | Kensey . |
| 4,750,492 | 6/1988 | Jacobs ..................................... 606/232 |
| 4,778,468 | 10/1988 | Hunt et al. . |
| 4,790,303 | 12/1988 | Steffee . |
| 4,858,603 | 8/1989 | Clemow et al. . |
| 4,873,976 | 10/1989 | Schreiber . |
| 4,889,110 | 12/1989 | Galline et al. . |
| 4,895,148 | 1/1990 | Bays et al. . |
| 4,927,421 | 5/1990 | Goble et al. . |
| 4,946,462 | 8/1990 | Watanabe . |
| 4,981,149 | 1/1991 | Yoon et al. . |
| 5,002,562 | 3/1991 | Oberlander . |
| 5,037,422 | 8/1991 | Hayhurst et al. . |
| 5,041,129 | 8/1991 | Hayhurst et al. . |
| 5,053,046 | 10/1991 | Janese . |
| 5,053,047 | 10/1991 | Yoon . |
| 5,059,206 | 10/1991 | Winters . |
| 5,102,421 | 4/1992 | Anspach, Jr. . |
| 5,127,412 | 7/1992 | Cosmetto et al. . |
| 5,141,520 | 8/1992 | Goble . |
| 5,154,189 | 10/1992 | Oberlander . |
| 5,156,616 | 10/1992 | Meadows et al. . |

FOREIGN PATENT DOCUMENTS

| 0390613 | 10/1990 | European Pat. Off. . |
|---|---|---|
| 0513736 | 11/1992 | European Pat. Off. . |
| WO8701270 | 3/1987 | WIPO . |

OTHER PUBLICATIONS

Cannon, Jr., Arthroscopic Meniscal Repair, Operative Arthroscopy, Chapter 16, (Raven Press 1991).

Primary Examiner—Gary Jackson

[57] ABSTRACT

A soft tissue repair system and method are provided. The soft tissue repair system includes a barbed suture anchoring member attached to at least one suture member. A suture retaining member engages the suture member such that the length and tension of the suture may be selectively adjusted before the suture is permanently engaged in the retaining member. In use, the barbed suture anchoring member and suture member are inserted into the soft tissue repair site and across a tear. The suture member extends back through the original entry side of the tear. A retaining member is applied to the suture member followed by tensioning of the suture member to draw the sides of the tear into apposition. Following tensioning, the retaining member is permanently affixed to the suture member to maintain the selected tension and length of the suture member.

6 Claims, 4 Drawing Sheets

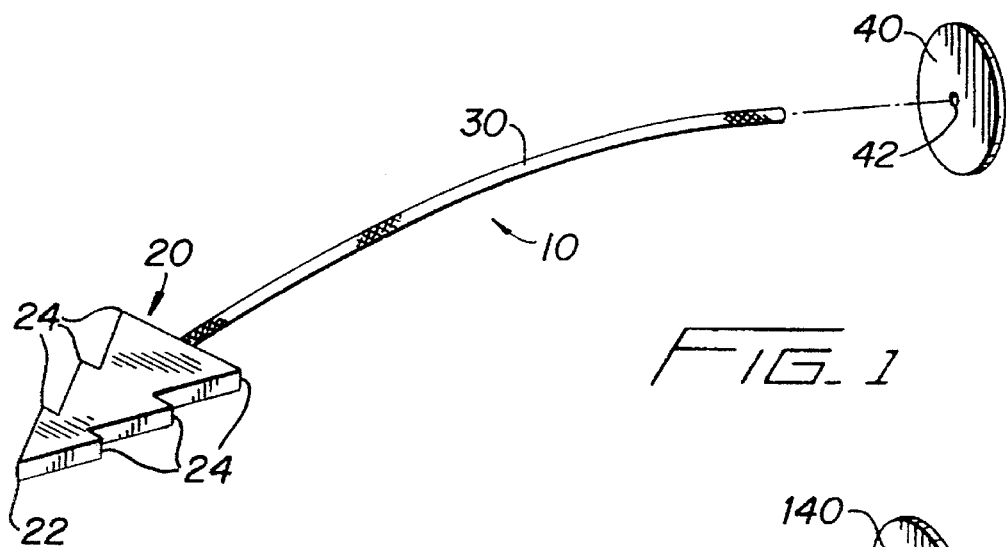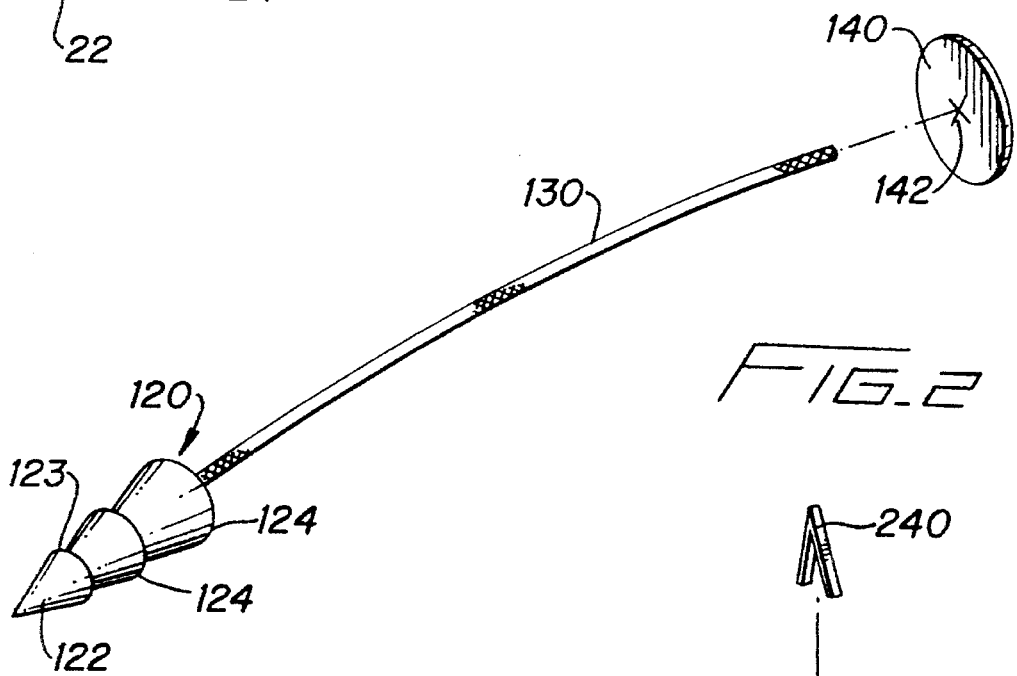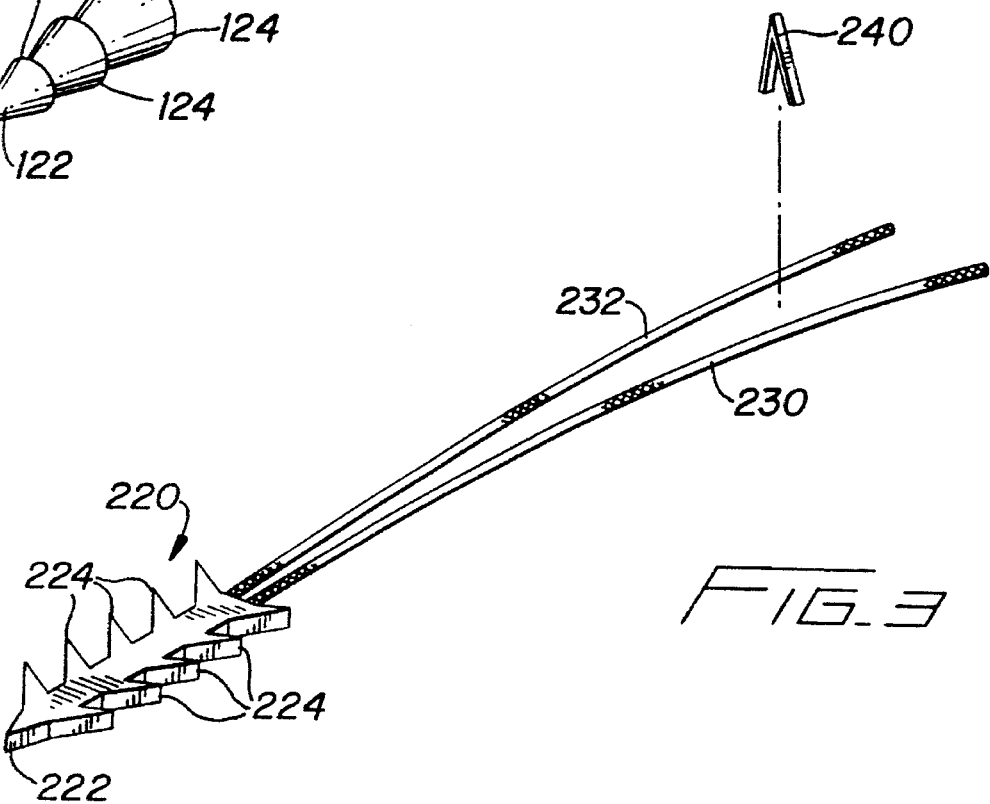

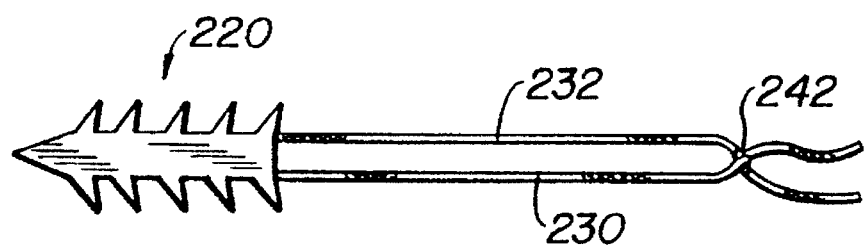
FIG_3A
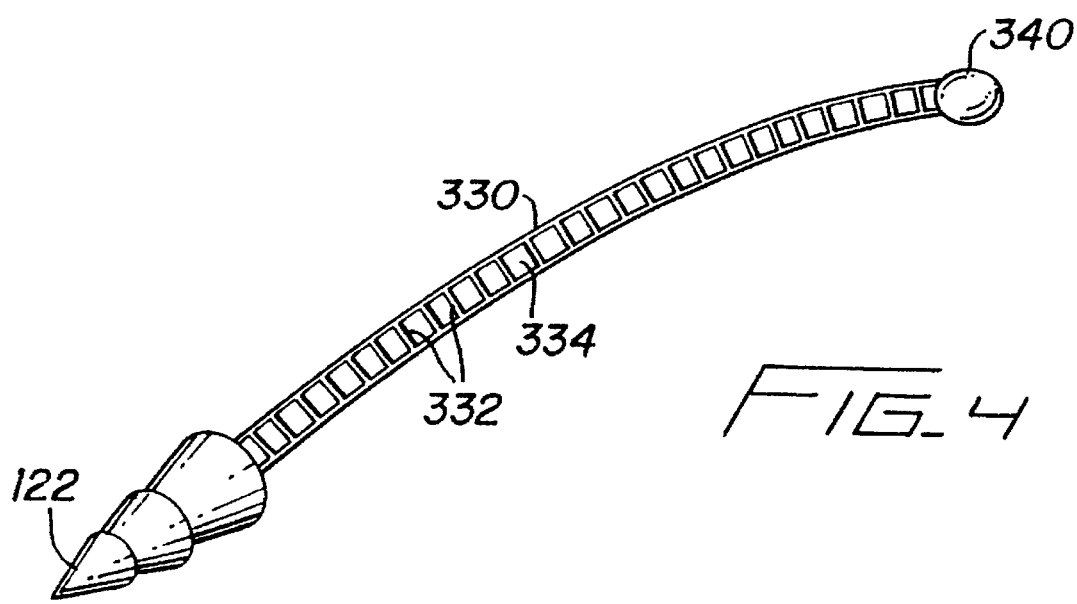
FIG_4
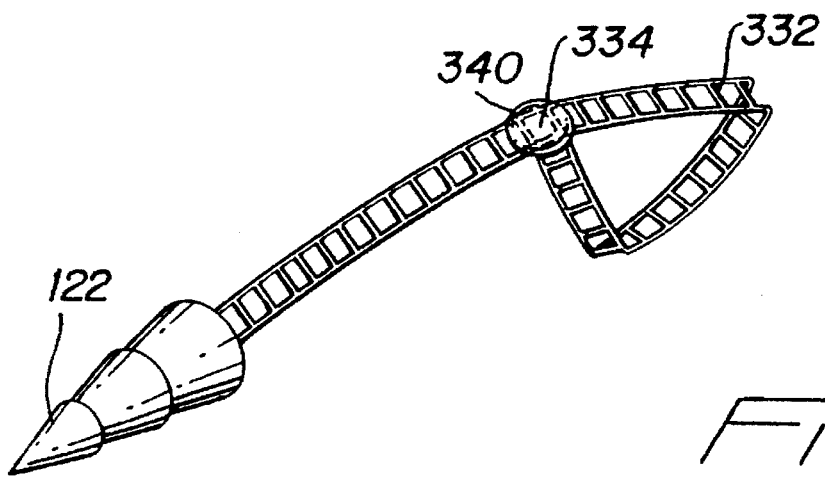
FIG_5

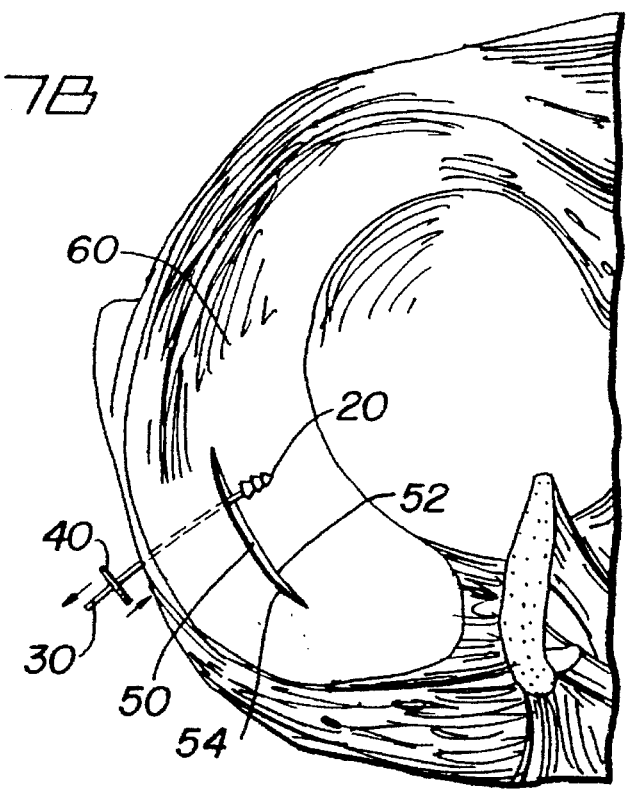
FIG_7B
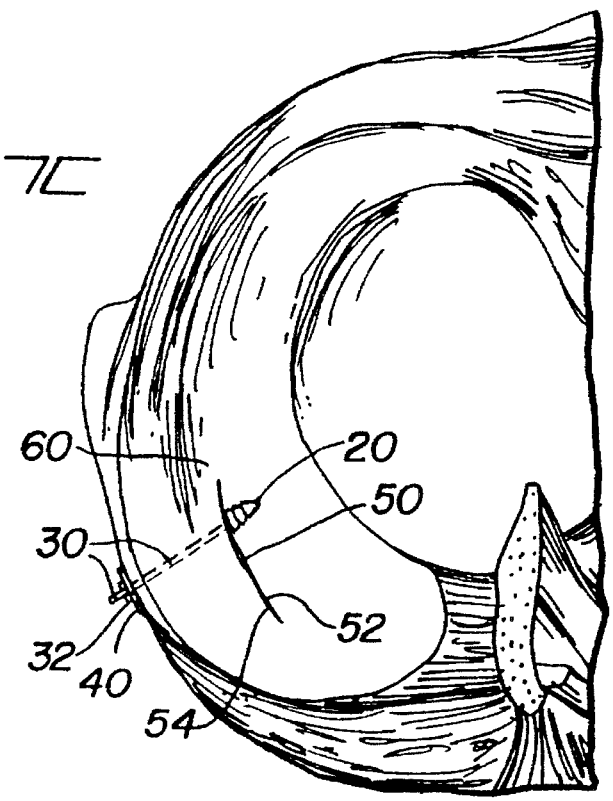
FIG_7C

SOFT TISSUE REPAIR SYSTEM AND METHOD

BACKGROUND OF THE INVENTION

1. Field of the Invention

The present invention relates to a system and method for repairing soft tissue and, more particularly, to a system and method for repairing torn meniscal tissue.

2. Background of the Invention

The surgical repair of soft tissue has typically been performed through incisions in the body to expose the area under repair followed by the application of sutures, staples, or other surgical fasteners. The use of such conventional devices typically requires a highly skilled surgeon to perform the repair and complete immobilization of the surgical area following the repair procedure. More recently, the use of arthroscopic and endoscopic techniques and equipment has reduced the size and depth of the incision required to perform the repair.

Surgical repair of cartilage and muscle adjacent a joint such as the knee often requires a high degree of skill on the part of the surgeon to reduce damage to adjacent nerves, blood vessels, cartilage, muscles, and tendons. In particular, the repair of the fibrocartilage disks within the knee known as the menisci, attached peripherally to the joint capsule, requires precision to avoid such damage.

In the past, meniscal surgery has included procedures for partial to complete removal of a torn meniscus, as well as attempts to surgically suture, staple, or fasten the tear in the meniscus to allow for healing. Other techniques have included removal of portions of the meniscus to arrest the spread of the tear.

Several devices and procedures have been proposed for the repair of meniscal tissue, especially the meniscus of the knee. In one arthroscopic procedure, a pair of surgical needles are inserted through cannulae into the knee on opposite sides of the tear in the meniscus to be repaired. The needles are linked by a single suture which is pushed down through the cannulae and across the tear. An incision is made in the skin at the point where the needles exit the knee joint so that the leading edge of each needle may be grasped and pulled through the joint. After the needles are removed, the ends of the sutures are tied outside the skin so that a horizontal suture is created in the meniscus. This time-consuming procedure is repeated for the placement of as many sutures as necessary to repair the meniscal tear.

U.S. Pat. No. 4,873,976 to Schreiber discloses surgical fasteners for repairing tears in body tissue, particularly the meniscus of the knee joint. The fastener has a base member for seating against the body tissue, a shaft upstanding from the base member for inserting into the tissue and across the tear, and at least one barb for locking the shaft in place, holding both sides of the tear together. The Schreiber fastener is a single unit, i.e., a one-piece prefabricated element of predetermined dimensions. As such, the shaft portion which is inserted across the tear has a fixed length which cannot be modified to provide adjustable sizing or tensioning across the tear.

Other fasteners for repairing a torn meniscus are shown in U.S. Pat. Nos. 5,059,206 and 4,895,148. Like the faster shown in the Schreiber patent, these fasteners do not provide means for adjusting length or the tension across the meniscal tear.

U.S. Pat. No. 4,741,330 to Hayhurst describes a method and apparatus for anchoring and manipulating cartilage within a joint during arthroscopic surgery. In Hayhurst, the cartilage is pierced by a hollow needle containing an elongate anchoring device with an attached suture. The suture passes through the bore of a hollow tube, positioned within the hollow needle behind the anchoring device. The tube is used to push the anchoring device out of the needle tip behind the cartilage to be anchored. In this manner, the anchoring device is intended to lodge in or beyond the cartilage at a nonparallel angle to the suture, thereby anchoring the suture to the cartilage. The needle and the tube may be withdrawn and the cartilage manipulated by appropriate tension on the suture. This device suffers from the disadvantage that the elongate anchoring device must change position during insertion into the cartilage from a first orientation within the hollow needle to a second orientation in the tissue.

In a separate embodiment, the Hayhurst patent describes a device for anchoring a suture to bone. Barb-like projections are provided on the exterior of an anchoring device to which is attached a suture. The anchoring device is inserted into a pre-drilled hole in bone to which tendons or ligaments are to be attached. A retainer including resilient suture-engaging edges and corners is slidable along the suture in one direction and grips the suture to resist sliding of the retainer in the opposite direction. Because a hole must be drilled in the bone prior to the insertion of the anchor, this device is not useful for repairing tears in soft body tissue.

There is a need in the art for a system for repairing soft tissue which comprises a suture anchoring member having a suture member attached thereto which is inserted across torn tissue without the need to change the orientation of the anchoring member. The system, preferably dimensioned and configured for arthroscopic and endoscopic use, should include a retaining member for retaining the end of the suture member opposite the suture anchoring member. There is a further need in the art for a system for repairing soft tissue in which a suture member attached to an anchoring member is adjustably engageable with a suture retaining member so that the length and tension of the suture member may be selected by the user during the surgical procedure. Such a system could be used for repairing soft tissue, especially in hard to access regions of the body such as the meniscus of the knee joint.

SUMMARY OF THE INVENTION

The present invention provides a novel system and method for repairing soft tissue. In particular, the present invention provides a novel system for repairing torn cartilage such as the meniscus of the knee joint. The system of the present invention is adaptable for arthroscopic and endoscopic use, advantageously reducing trauma through minimal invasion at the site of the repair.

The novel soft tissue repair system provides a barbed suture anchoring member attached to at least one suture member. A suture retaining member engages the suture member such that the length and tension of the suture may be selectively adjusted before the suture is permanently engaged in the retaining member.

The barbs of the barbed suture anchoring member are tapered in the direction of insertion to facilitate insertion and to inhibit pullout of the device following insertion. Preferably, the anchoring member, suture member, and suture retaining member are all fabricated from bioabsorbable materials. The absorption rate of the bioabsorbable materials is selected to allow sufficient time for healing.

In use, the soft tissue repair system of the present invention involves inserting the barbed suture anchoring member and suture member into the soft tissue repair site and across a tear. The barbed anchoring member is embedded in tissue on one side of the tear while the suture member extends back through the original entry side of the tear. A retaining member is applied to the suture member followed by tensioning of the suture member to draw the sides of the tear into apposition. Following tensioning, the retaining member is permanently affixed to the suture member to maintain the selected tension and length of the suture member.

BRIEF DESCRIPTION OF THE DRAWINGS

FIG. 1 is a perspective view of a preferred embodiment of a soft tissue repair system of the present invention.

FIG. 2 is a perspective view of another preferred embodiment of a soft tissue repair system of the present invention.

FIGS. 3 and 3A are perspective views of another preferred embodiment of a soft tissue repair system of the present invention.

FIG. 4 is a perspective view of another preferred embodiment of a soft tissue repair system of the present invention.

FIG. 5 is a perspective view of the soft tissue repair system of FIG. 4 with the suture retaining member engaged with the suture member.

FIGS. 7A, 7B, and 7C illustrate a soft tissue repair system of the present invention used to repair a tear in the meniscus of the human knee.

DETAILED DESCRIPTION OF THE PREFERRED EMBODIMENTS

Figure 6:
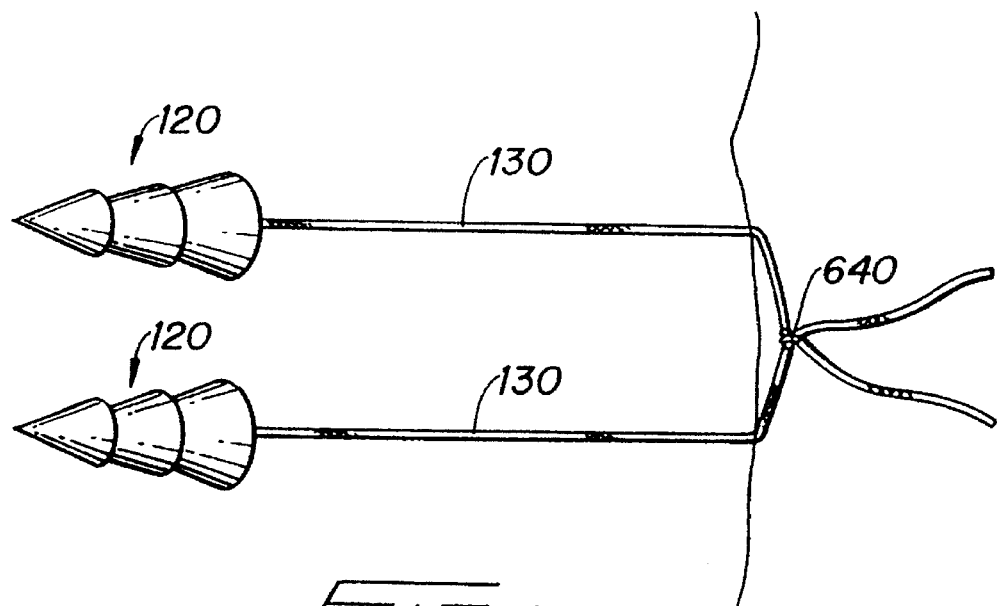
FIG. 6 is a perspective view of another preferred embodiment of a soft tissue repair system of the present invention.

Referring now in specific detail to the drawings, in which like reference numerals identify similar or identical elements throughout the several views, FIG. 1 depicts a preferred embodiment of a soft tissue repair system of the present invention. As used herein, the term "soft tissue" refers to all of the non-bony tissues within an organism including, but not limited to, muscle, cartilage, skin, etc. The term "tear" refers to any abnormal separation in soft tissue such as that resulting from injury, disease, surgical incision, etc.

Repair system 10 generally comprises barbed suture anchoring member 20, having a generally triangular-shaped sharp tip 22 at a distal end to facilitate insertion and penetration into soft tissue. Barbs 24 are located proximal to tip 22 and project outwardly from the anchor. The barbs 24 taper toward the distal insertion end of the suture anchor, forming a suture anchoring member having a planar, generally triangular-shaped tip with a series of truncated triangular sections extending proximally from the tip. Each of the truncated triangular sections preferably has a base portion larger than the base portion of the preceding section. The triangular sections may be planar, as illustrated in FIG. 1.

Alternatively, the sections extending from tip 22 may have a frustoconical shape, each frustoconical section having a larger base than the preceding section and coaxially aligned with tip 22. These configurations allow the barbed suture anchor to easily penetrate tissue during insertion across the tissue and inhibit pullout of the device following insertion.

A suture member 30 is secured to the barbed suture anchoring member 20. In the embodiment of FIG. 1, the suture member is a single, flexible, braided suture. However, it is contemplated that the suture member be selected from any of the known suture materials or any elongate, biocompatible material capable of attachment to the barbed suture anchoring member. It is further contemplated that the suture member may comprise a plurality of elongated members.

Suture member 30 may be attached to the barbed suture anchor 20 through a variety of conventional fastening techniques including adhesive bonding, crimping, swaging, and the like. Alternatively, anchoring member 20 may include a loop within its interior through which the suture may pass. It is contemplated that the suture anchoring member may be formed with the suture member as a single unit, e.g., during a molding formation process.

Suture retaining member 40 is used to engage suture member 30 such that the length and tension of the suture member may be selected by the user during closure of the tissue. In this embodiment, the suture retaining member is configured as a disk-shaped button having an aperture 42. The term "button" is used herein to broadly encompass any device adapted to retain a suture member. Preferably, aperture 42 has a circular cross-section, the diameter of which is less than or equal to the diameter of the suture member 30. Such a configuration aids in the retention of the suture member in the aperture.

Suture member 30 passes through aperture 42 of the suture retaining member. The suture member is pulled outwardly while pressing down on the suture retaining member. In this manner, the desired length and tension of the suture member may be achieved for optimal tear closure. The suture member is fixedly engaged in the suture retaining device in any known manner such as knotting, clipping, etc. Alternatively, the suture member may be formed having a series of generally spherical projections, the diameter of the spheres being slightly larger than the diameter of the aperture. The spheres thus serve to retain the suture member within the suture retaining member.

FIG. 2 illustrates another embodiment of the soft tissue repair system of the present invention. In this embodiment, barbed anchoring member 120 has a pointed conical tip 122 formed on a distal end. A series of frustoconical sections 124 sequentially extends proximally from the tip 123, each frustoconical section having a larger base than the preceding section and coaxially aligned with conical tip 122.

Suture member 130, illustrated as a braided suture as in the previous embodiment, is secured to barbed anchoring member 120 through any of the techniques previously discussed with respect to the soft tissue repair system of FIG. 1.

Suture retaining member 140 is configured as a disk-shaped button, similar to retaining member 40 of the previous embodiment. In this embodiment, retaining member 140 is provided with suture gripping aperture 142. Gripping aperture 142 is formed by the intersection of two mutually perpendicular slits in button 140 which permits the suture to be pulled through in one direction but prevents movement in the opposite direction. This configuration permits the user to pull suture member 130 through the aperture and adjust the length and tension of the suture without the need to apply additional retaining means, e.g. a knot or clip, to the suture member following tensioning.

FIG. 3 illustrates another embodiment of the soft tissue repair system of the present invention. In this embodiment, barbed suture anchoring member 220 comprises a pointed planar portion 222 having a plurality of barbs 224 extending from either side. The longitudinal axes of barbs 224 form an acute angle with the longitudinal axis of planar portion 222, permitting easy insertion into the tissue and across the tear and inhibiting movement in the opposite direction.

In this embodiment, suture member 230 illustratively comprises of a pair of sutures 232 each secured to the barbed suture anchoring member 220 by any of the methods described in the previous embodiments. Although the suture member is illustrated as a pair of sutures, it is contemplated that more than two sutures, or a single suture as in the previous embodiments, may be used with barbed anchoring member 220.

Suture retaining member 240 comprises a clip adapted to hold both suture members 232 following tensioning. The clip may be used alone or in conjunction with the disk-shaped button retaining members of the first two embodiments. Alternatively, it is contemplated that the suture retaining member for a barbed anchoring member having a plurality of sutures attached thereto may comprise another adjacent suture. In FIG. 3A, suture member 232 is the suture retaining member for suture member 230 and suture member 230 is the suture retaining member for suture member 232. Knot 242, formed by tying the ends of the sutures together, unites the two suture members, permitting the adjacent suture member to function as a suture retaining member.

FIG. 4 illustrates another embodiment of the soft tissue repair system of the present invention. This embodiment employs barbed anchoring member 120, as in the embodiment of FIG. 2, having suture member 330 attached thereto. Suture member 330 is integrally formed with suture retaining member 340, a generally spherical projection extending from the proximal end of suture member 330. Apertures 334, having a cross-sectional area smaller than that of the cross-sectional area of suture retaining member 340, are formed in suture 330 through the provision of multiple rails 332.

To retain the suture member in a desired position, suture retaining member 340 is force fit through an aperture 332 at the desired position along suture member 330, depicted in FIG. 5.

FIG. 6 illustrates a further embodiment of the soft tissue repair system of the invention. A pair of barbed anchoring members 120 having suture members 130 attached thereto are employed. When inserted across a soft tissue defect such as a tear, the suture member of one anchoring member serves as the suture retaining member of the other anchoring member, such as by forming knot 640 from the two suture members as shown in FIG. 6.

Preferably, both the suture anchoring member and the suture member are fabricated from bioabsorbable materials. Such materials include homopolymers and copolymers of lactide, glycolide, polydioxanone, trimethylene carbonate, polyethylene oxide or other bioabsorbable materials or blends of these homopolymers or copolymers. One material preferred for construction of the barbed suture anchoring member and the suture member comprises a copolymer of lactide and glycolide of approximately 82% lactide and 18% glycolide. As appreciated by those skilled in the art, the bioabsorbable materials may be selected such that the absorption rate is matched to the needs of the particular soft tissue repair application. Thus, the elements of the tissue repair system will remain in the body only for so long as necessary to heal the soft tissue. The suture retaining member may be selected from the above-identified bioabsorbable materials or, in applications where the retaining member is positioned outside the body, may be selected from any biocompatible material.

Figure 7A:
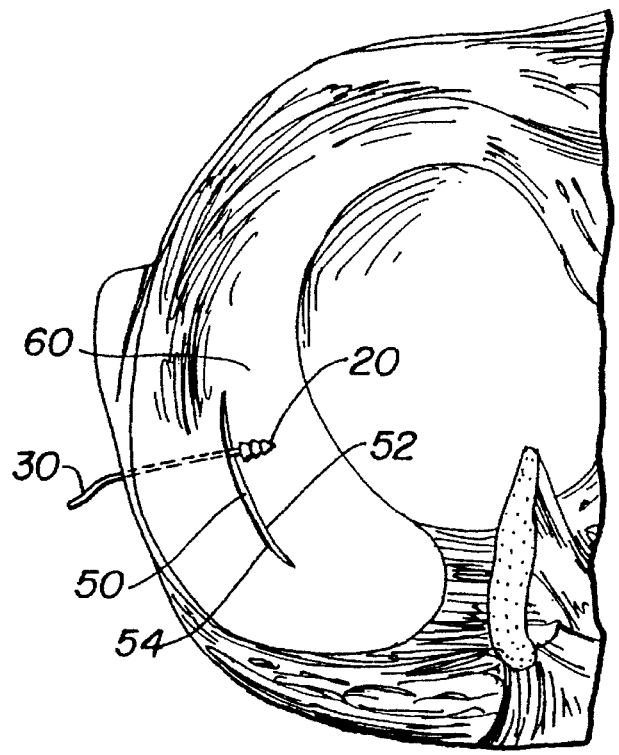

The use of the tissue repair system of the present invention is illustrated in FIGS. 7A–7C which demonstrate the repair of a tear in the meniscus of the knee joint. It is understood that, although illustrated for use with a meniscal tear, the repair system of the present invention may advantageously be employed to repair soft tissue throughout the body. During arthroscopic surgery, the barbed suture anchoring member with the suture retaining means attached thereto will be inserted through a cannula to the site of the meniscal tear. To aid in insertion, a suture anchor applicator may be employed (not shown). The applicator may be in the form of a hollow cylinder configured to receive the barbed suture anchor at its distal end. The suture member passes through the bore of the cylinder, exiting at its proximal end. When the suture anchor is cannulated, the suture member is preferably offset from the longitudinal axis of the suture anchor.

The barbed suture anchor 20 is inserted into the meniscus of the knee 60, perpendicular to and across the tear 50, illustrated in FIG. 7A. The barbed suture anchor 20 is preferably positioned with the entire barbed portion contained within the meniscal tissue on the distal side 52 of the tear, i.e., the side of the tear furthest from the initial point of insertion. In this position, the suture member 30 extends from barbed suture anchor 20, across the tear, through the insertion tool and cannula, to a position outside the meniscus of the knee.

To close the meniscal tear, the suture member 30 is tensioned, drawing proximal side 54 and distal side 52 of tear 50 into apposition as shown in FIG. 7B. In the embodiments employing disk-shaped button 40 as the suture retaining member, the suture member is engaged within the button aperture prior to tensioning. As the suture member 30 is pulled, button 40 may be pressed against a surface exterior to the meniscus of the knee to aid in the tensioning process. The length of the suture member contained within the meniscus of the knee is fixed when the suture member is fixedly engaged in the suture retaining member as by knotting, clipping, or through the use of a gripping aperture as shown in the tissue retaining member of FIG. 2.

In FIG. 7C, suture member 30 has been fully tensioned and sides 52 and 54 of the meniscal tear have been drawn together. Suture member 30 is fixedly engaged in suture retaining member 40 through knot 32 or by clipping. Unwanted extra length of suture member 30 is removed by cutting. In this manner, a tissue repair system is achieved in which the length and tension of the suture member is custom matched to the size and position of the tear within the body. Depending upon the size of the tear, plural tissue repair systems may be employed, each system being deployed as described above with reference to FIGS. 7A–7C.

While the invention has been particularly shown and described with reference to the preferred embodiments, it will be understood by those skilled in the art that various modifications and changes in form and detail may be made without departing from the scope and spirit of the invention. Accordingly, modifications such as those suggested above, but not limited thereto, are to be considered within the scope of the invention.

What is claimed is:

1. A system for repairing soft tissue comprising:

a barbed suture anchoring member configured and dimensioned to be retained within soft tissue, wherein said barbed suture anchoring member has proximal and distal ends and comprises a pointed distal tip portion having a base, and a series of following sections extending proximally from the base of said distal tip portion, each following section having a larger base than the preceding section;

at least one suture member attached to said barbed suture anchoring member, said suture member integrally comprising two elongated members connected by a plurality of cross rails which are spaced apart so as to define a series of apertures, said suture member having a distal end attached to said barbed suture anchoring member and a proximal end portion; suture retaining structure for engaging said at least one suture member, said suture retaining structure comprising an insertion member attached to said proximal end portion of said at least one suture member, said insertion member being insertable through at least one of said apertures of said suture member, said insertion member being configured and dimensioned to resist withdrawal.

2. A system for repairing soft tissue according to claim 1 wherein said barbed suture anchoring member is dimensioned and configured to be inserted through an arthroscopic cannula.

3. A system for repairing soft tissue according to claim 1 wherein said distal tip portion is conical and said following sections are frustoconical.

4. A system for repairing soft tissue according to claim 1 wherein said barbed suture anchoring member is bioabsorbable.

5. A system for repairing soft tissue according to claim 1 wherein said suture member is bioabsorbable.

6. A system for repairing soft tissue according to claim 1 wherein said suture retaining structure is bioabsorbable.

* * * * *